United States Patent [19]
McCullough et al.

[11] Patent Number: 5,962,714
[45] Date of Patent: Oct. 5, 1999

[54] MONOCYCLOPENTADIENYL TRANSITION METAL CATALYST AND OLEFIN POLYMERIZATION PROCESS

[76] Inventors: Laughlin Gerard McCullough, 105 Lakewood Dr., Longview, Tex. 75604-1401; James C.W. Chien, 15 Coach La., Amherst, Mass. 01002; Juan Carlos Flores, C/ Yánguas 2,3º C, Madrid - E28803, Spain; Marvin D. Rausch, 300 Alpine Dr., Amherst, Mass. 01002

[21] Appl. No.: 08/725,036

[22] Filed: Oct. 2, 1996

Related U.S. Application Data

[60] Provisional application No. 60/004,717, Oct. 2, 1995.

[51] Int. Cl.⁶ .................. C07F 7/10; C07F 17/00
[52] U.S. Cl. .................. 556/11; 556/9; 556/13; 556/19; 556/20; 556/51; 556/52; 556/53; 502/117; 502/152; 502/155; 526/127; 526/160; 526/943
[58] Field of Search .................. 556/9, 11, 13, 556/19, 20, 51, 52, 53; 502/117, 152, 155

[56] References Cited

U.S. PATENT DOCUMENTS

| | | |
|---|---|---|
| 2,827,447 | 3/1958 | Nowlin et al. . |
| 2,864,843 | 12/1958 | Witt et al. . |
| 2,911,424 | 11/1959 | Kaufman . |
| 3,161,629 | 12/1964 | Gorsich . |
| 4,404,344 | 9/1983 | Sinn et al. . |
| 4,542,199 | 9/1985 | Kaminsky et al. . |
| 4,752,597 | 6/1988 | Turner . |
| 4,978,730 | 12/1990 | Maezawa et al. . |
| 5,023,222 | 6/1991 | Maezawa et al. . |
| 5,026,798 | 6/1991 | Canich . |
| 5,045,517 | 9/1991 | Campbell, Jr. et al. . |
| 5,055,438 | 10/1991 | Canich ........................ 502/117 |
| 5,064,802 | 11/1991 | Stevens et al. ................ 502/155 |
| 5,066,741 | 11/1991 | Campbell, Jr. . |
| 5,132,380 | 7/1992 | Stevens et al. . |
| 5,196,490 | 3/1993 | Campbell, Jr. et al. . |
| 5,198,401 | 3/1993 | Turner et al. . |
| 5,218,071 | 6/1993 | Tsutsui et al. . |
| 5,272,236 | 10/1991 | Lai et al. ..................... 526/348.5 |
| 5,278,119 | 1/1994 | Turner et al. . |
| 5,278,272 | 1/1994 | Lai et al. . |
| 5,279,999 | 1/1994 | DeBoer et al. . |
| 5,324,800 | 6/1994 | Welborn, Jr. et al. . |
| 5,340,892 | 8/1994 | Kuramoto . |
| 5,350,723 | 9/1994 | Neithamer et al. . |
| 5,372,682 | 12/1994 | Devore et al. . |
| 5,372,980 | 12/1994 | Davis . |
| 5,374,700 | 12/1994 | Tsutsui et al. . |
| 5,399,635 | 3/1995 | Neithamer et al. . |
| 5,453,410 | 9/1995 | Kolthammer et al. . |
| 5,453,475 | 9/1995 | Rieger et al. . |
| 5,554,795 | 9/1996 | Frey et al. . |
| 5,563,284 | 10/1996 | Frey et al. ...................... 556/53 |
| 5,565,396 | 10/1996 | Frey et al. . |
| 5,578,741 | 11/1996 | Frey et al. . |
| 5,599,885 | 2/1997 | Kawasaki et al. . |

FOREIGN PATENT DOCUMENTS

WO 96/13529  5/1996  WIPO .

OTHER PUBLICATIONS

J. Organomet. Chem., vol. 423, p. 31, 1992.
Organometallics 1994 American Chemical Society, 13, 4140 Title: {[2–(Dimethylamino)ethyl] cyclopentadienyl}trichlorotitanium: A New type of Olefin Polylmerization Catalyst by Juan Carlos.
Organometallics, "{[2–(Dimethylsmino)ethyl] cyclopentadienyl}trichlorotitanium: A new type of olefin Polymerization catalyst", Flores et al. Jul. 1994.
Hawley's Condensed Chemical Dictionary, 5th Edition, p. 749, 1987.
Chem. Rev. 1992, 92, pp. 965–994, "Synthesis and Applications of Chiral Cyclopentadienylmetal Complexes", Ronald L. Halterman, 1992.
Flores et al. "{[2–(Dimethylamion)ethyl] cyclopentadienyl}trichloro titanium: A new type of olefin polymerization catlyst", Advance ACS abstracts, 122,32131x, Oct. 1994.

*Primary Examiner*—David W. Wu

[57] ABSTRACT

Disclosed is a monocyclopentadienyl metal compound that can polymerize polyolefins as part of a catalyst system. The monocyclopentadienyl compound can specifically be $(C_5H_4CH_2CH_2NMe_2)TiCl_3$.

20 Claims, No Drawings

MONOCYCLOPENTADIENYL TRANSITION METAL CATALYST AND OLEFIN POLYMERIZATION PROCESS

This application claims provisional of application 60/004,717 filed Oct. 2, 1995.

FIELD OF THE INVENTION

The present invention relates to monocyclopentadienyl transition metal catalysts. The present invention further relates to a monocyclopentadienyl transition metal catalyst system and a method to produce polyolefins such as polyethylene and polypropylene.

BACKGROUND OF THE INVENTION

Many catalytic processes exist for the polymerization or copolymerization of olefins such as ethylene and propylene. These processes have traditionally utilized a Ziegler-Natta catalyst system. These catalyst systems contain a transition metal compound (typically a titanium, zirconium, or vanadium halide or alkoxide) and a main group metal alkyl (usually an aluminum alkyl). The Ziegler-Natta catalyst systems are heterogeneous and possess a number of different active catalyst sites. Each different active site has different characteristics and produces a different polymer, and as a result, Ziegler-Natta catalyst systems produce polyolefins with broad molecular weight distributions and copolymers with broad compositional distributions.

Recent developments in the field of olefin polymerization have focused on the use of transition metal compounds having at least one π-bound cyclopentadienyl ligand. The cyclopentadienyl ligand can be substituted or unsubstituted, and generally includes fused ring derivatives such as indenyl and fluorenyl. These cyclopentadienyl transition metal compounds are often referred to as metallocenes, though the term was initially used to describe biscyclopentadienyl compounds such as dicyclopentadienyliron (ferrocene).

Olefin polymerization systems using metallocenes differ from Ziegler-Natta catalyst systems in important ways. With metallocene catalysts there is generally only one catalytically active species responsible for the polymerization of the monomers. The metallocenes, therefore, produce uniforms chains of polymer having narrower molecular weight distributions and narrower compositional distribution. Metallocene catalysts are also typically much more active on a weight basis than Ziegler-Natta catalysts. Metallocene catalysts can be 10 to 1,000 times more active than the best Ziegler-Natta catalysts.

Metallocene catalysts are often classified into two separate groups, those possessing one cyclopentadienyl ligand, and those possessing two cyclopentadienyl ligands. The monocyclopentadienyl metallocenes are generally known in the art as good styrene polymerization catalysts and poor olefin polymerization catalysts, whereas biscyclopentadienyl metallocenes are generally known in the art as good olefin polymerization catalysts and poor styrene polymerization catalysts. Representative examples of these various catalysts are disclosed in U.S. Pat. Nos. 4,978,730; 5,023,222; 5,045,517; 5,066,741; 5,196,490; and 5,340,892 disclosing monocyclopentadienyl metallocenes. Examples of biscyclopentadienyl metallocenes are disclosed in U.S. Pat. Nos. 4,404,344; 4,542,199; 4,752,597; 5,198,401; 5,278,119; and 5,453,475.

Despite the utility of the catalysts disclosed above, a need still exists to discover more useful and efficient catalysts to polymerize olefins.

SUMMARY OF THE INVENTION

According to the present invention, a novel composition is provided that comprises a monocylopentadienyl transition metal compound of the formula:

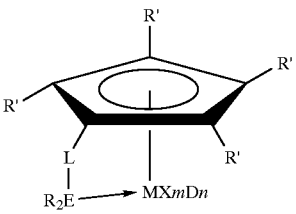

Wherein,

M is a Group IV metal selected from the group consisting of titanium, zirconium, and hafnium;

m is one, two, or three, depending on the valency and oxidation state of M;

R' is each independently selected from the group consisting of hydrogen, substituted hydrocarbyl groups, unsubstituted hydrocarbyl groups, silyl groups, germyl groups, and stannyl groups, including wherein two or more R' groups can be joined to form a ring;

L is a covalent bridging group containing a main group element from Group 14 selected from the group consisting of carbon, silicon, germanium, and tin.

E is datively bonded to M, and is a main group element from Group 15 selected from the group consisting of nitrogen, phosphorous, arsenic, and antimony;

R is each independently selected from the group consisting of substituted hydrocarbyl groups, unsubstituted hydrocarbyl groups, and silyl groups, wherein two R-groups can be joined to form a ring, and wherein an L group and R can be joined to form a ring;

X is each independently selected from the group consisting of hydrogen, halides, substituted hydrocarbyl groups, unsubstituted hydrocarbyl groups, silyl groups, alkoxides, aryloxides, amides, arylamides, phosphides, arylphosphides, carboxylates, and sulfonates;

D is a neutral Lewis base; and n is 0, 1, or 2.

The present invention is also directed towards a catalyst system that comprises (A) a monocyclopentadienyl compound described above, and (B) an activator chosen from (1) alumoxanes, (2) a salt of a labile, relatively non-coordinating anion that is able to abstract one substituent X from the monocyclopentadienyl compound, and (3) a neutral Lewis acid that can abstract one substituent X from the monocyclopentadienyl compound.

The present invention is also directed towards a polymerization process incorporating the above catalyst system for producing polyolefins comprising the steps of (i) contacting an olefin monomer at a temperature and pressure sufficient to produce a polymer with the catalyst system described above, and (ii) recovering a polyolefin.

DETAILED DESCRIPTION OF THE INVENTION

The applicants have unexpectedly discovered a novel monocyclopentadienyl transition metal compound that is very useful in catalyst systems for the polymerization of polyolefins. These catalyst systems employing the monocyclopentadienyl transition metal compound are unexpectedly active for the polymerization of olefins. This is particularly unexpected since monocyclopentadienyl transition metal compounds are generally useful for the polymerization of bulky monomers such as styrene, and are poor olefin polymerization catalysts. These monocyclopentadienyl transition metal compound catalyst systems are unexpectedly active in the polymerization of olefins, comparable to, or better than some biscyclopentadienyl transition metal catalyst systems.

It is generally accepted that the active species in both the monocyclopentadienyl transition metal compounds and biscyclopentadienyl transition metal compounds is a cation. These cations are strong Lewis acids, capable of coordinating Lewis bases, such as ethers or amines. U.S. Pat. No. 5,198,401 teaches this, and further states that the coordination of Lewis bases is undesirable and leads, at best, to catalysts of very low activity. It is therefore very unexpected that the intramolecular coordination of a Lewis base would produce a catalyst system of high activity, which is the exact result of the presently claimed compound and process.

The monocyclopentadienyl transition metal compound of the present invention entails:

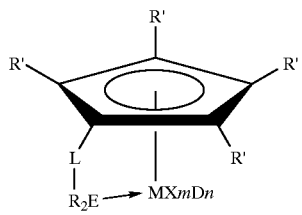

Wherein,

M is a Group IV metal selected from the group consisting of titanium, zirconium, and hafnium;

m is one, two, or three, depending on the valency and oxidation state of M;

R' is each independently selected from the group consisting of hydrogen, substituted hydrocarbyl groups, unsubstituted hydrocarbyl groups, silyl groups, germyl groups, and stannyl groups, including wherein two or more R' groups can be joined to form a ring;

L is a covalent bridging group containing a main group element from Group 14 selected from the group consisting of carbon, silicon, germanium, and tin.

E is datively bonded to M, and is a main group element from Group 15 selected from the group consisting of nitrogen, phosphorous, arsenic, and antimony;

R is independently selected from substituted hydrocarbyl groups, unsubstituted hydrocarbyl groups, and silyl groups, wherein two R-groups can be joined to form a ring, and wherein an R-group and L can be joined to form a ring;

X is each independently selected from the group consisting of hydrogen, halides, substituted hydrocarbyl groups, unsubstituted hydrocarbyl groups, silyl groups, alkoxides, aryloxides, amides, arylamides, phosphides, arylphosphides, carboxylates, and sulfonates;

D is a neutral Lewis base; and n is 0, 1, or 2.

The monocyclopentadienyl of the monocyclopentadienyl transition metal compound of the present invention contains a single cyclopentadienyl ligand that can be unsubstituted or substituted. This includes substituted cyclopentadienyl ligands in which the substituents form a fused aliphatic or aromatic ring or rings. This broad description thus includes monoindenyl transition metal compounds of the formula:

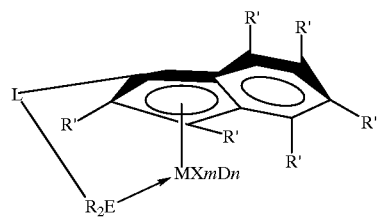

The monocyclopentadienyl transition metal compound also includes monofluorenyl transition metal compounds of the formula:

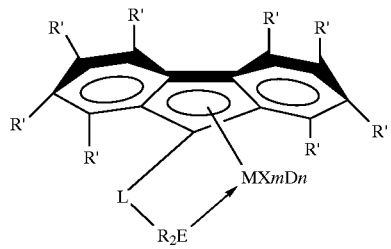

The transition metal M of the monocyclopentadienyl transition metal compound of the present invention is a Group IV metal and is selected from the group consisting of titanium, zirconium, and hafnium, more preferably titanium and zirconium, with titanium being most preferred. This Group IV of the periodic table seems to be the most active in metallocenes with titanium being the most preferred when in combination with the monocyclopentadienyl groups.

According to the present invention m is one, two, or three, depending upon the valency and oxidation state of M, as such, m is equal to the oxidation state of M minus one, unless M is charged and then m is two less than the oxidation state of M.

In the cyclopentadienyl transition metal compound of the present invention, m is preferably 2 or 3, however, m being three is most preferred.

In the composition according to the present invention, R' is each independently selected from the group consisting of hydrogen, substituted hydrocarbyl groups, unsubstituted hydrocarbyl groups, silyl groups, germyl groups, and stannyl groups, including wherein two or more R' groups can be joined to form a ring. Preferably, R' is each independently selected from the group consisting of hydrogen and $C_1$–$C_4$ alkyls, wherein at least one R' is preferably hydrogen, more preferably at least two R' are hydrogen. The applicants have unexpectedly discovered that when all R' are alkyls, the catalyst activity is significantly reduced. Therefore, at least one R' is preferably hydrogen.

In the monocyclopentadienyl transition metal compound of the present invention, L is a covalent bridging group containing a main group element from group 14 selected from the group consisting of carbon silicon, geraninum, and tin, with carbon being preferred. L is more preferably selected from the group consisting of $CR'_2$, $CR'_2CR'_2$, $CR'_2CR'_2CR'_2$, and $CR'=CR'$, preferably with $CH_2CH_2$ being most preferred. It is preferred that L not be too long of a chain, because then the $R_2E$ group attached thereto may not be easily coordinated to the metal M of the specific molecule to which the particular L is attached, leading to undesirable side reactions.

In the monocyclopentadienyl transition metal compound of the present invention, E is datively bonded to M, and is a main group element from Group 15 selected from the group consisting of nitrogen, phosphorous, arsenic, and antimony; preferably nitrogen and phosphorous, with nitrogen being most preferred.

The two R groups attached to E are each independently selected from the group consisting of: substituted hydrocarbyl groups, unsubstituted hydrocarbyl groups, and silyl groups, wherein two R-groups can be joined to form a ring, and wherein an R-group and L can be joined to form a ring. The two R-groups are each preferably hydrocarbyl groups with each R-group most preferably being methyl. When the R-groups, either together or independently, are too bulky, such as when both R-groups are isopropyl, the reactivity of the catalyst is reduced, thus, the R-groups need not be too bulky, and are preferably the size of an ethyl, group or smaller, with methyl being most preferred.

The X according to the present invention in the cyclopentadienyl transition metal compound is each independently selected from the group consisting of hydrogen, halides, substituted hydrocarbyl groups, unsubstituted hydrocarbyl groups, silyl groups, alkoxides, aryloxides, amides, arylamides, phosphides, arylphosphides, carboxylates, and sulfonates; with X being more preferably halides or alkoxides, with chlorine and isopropoxide being most preferred. The halides and alkoxides are more preferred X due to availability and cost.

In the monocyclopentadienyl transition metal compound according to the present invention, D is a neutral Lewis base; and is preferably selected from the group consisting of ether and tetrahydrofuran. However, since n can be zero, D is optional.

As stated above, n can be zero, one, two, or three, but is most preferably zero.

Examples of some specific monocyclopentadienyl metal compounds of the present invention include $(C_9H_6CH_2CH_2NMe_2)$ $TiCl_3$, $(C_5H_4CH_2CH_2NEt_2)$ $TiCl_3$, $(C_5H_4CH_2CH_2NMe_2)Ti(OCHMe_2)_3$, and $(C_5H_4CH_2CH_2NMe_2)TiCl_3$, with $(C_5H_4CH_2CH_2NMe_2)$ $TiCl_3$ being most preferred.

The catalyst system according to the present invention entails a catalyst system that comprises:

(A) a monocyclopentadienyl metal compound, as stated above; and (B) an activator selected from the group consisting of;
  (1) alumoxanes,
  (2) a salt of a labile, relatively non-coordinating anion that is able to abstract one substituent X from the compound of (A); and
  (3) a neutral Lewis acid that can abstract one substituent X from the compound of (A).

The catalyst system according to the present invention also can optionally include a main group organometallic compound (C) wherein the metal of the main group organometallic compound is selected from the group consisting of lithium, sodium, potassium, magnesium, calcium, zinc, boron, and aluminum. The main group organometallic compound is preferably selected from the group consisting of alkyl boranes, alkyl aluminums, and alkyl zincs, and more preferably trialkyl aluminums. The trialkyl aluminums are more preferred since they are better scavengers of adventitious impurities such as oxygen and water.

The catalyst system according to the present invention preferably entails an alumoxane B(1) that is methylalumoxane; and a salt of a labile, relatively non-coordinating anion, B(2) that is selected from the group consisting of borate salts and aluminate salts, and a neutral Lewis acid B(3) that is preferably selected from the group consisting of boranes and alanes. Specific examples of the borate salts and aluminate salts are triphenylcarbenium tetrakis(pentafluorophenyl) borate, triphenylcarbenium benzyltris(pentafluorophenyl) borate, triphenylcarbenium phenyltris(pentafluorophenyl) borate, triphenylcarbenium methyltris(pentafluorophenyl) borate, triphenylcarbenium tetrakis[3,5-bis(trifluoromethyl) phenyl]borate, triphenylcarbenium tetrakis(2,3,4,5-tetrafluorophenyl) borate, triphenylcarbenium tetrakis(2,3,5,6-tetrafluorophenyl)borate, triphenylcarbenium tetrakis(3,4,5-trifluorophenyl)borate, tropylium tetrakis(pentafluorophenyl)borate, tropylium tetrakis(pentafluorophenyl)aluminate and triphenylcarbenium tetrakis(pentafluorophenyl)aluminate. Specific examples of the boranes and alanes are tris(pentafluorophenyl)borane, tris[3,5-bis(trifluoromethyl)phenyl]borane, tris(2,3,4,5-tetrafluorophenyl)borane, tris(2,3,5,6-tetrafluorophenyl) borane, tris(pentafluorophenyl)alane, and tris[3,5-bis(trifluoromethyl)phenyl]alane.

The process for producing polyolefins according to the present invention comprises:

(i) Contacting at least one olefin at a temperature and pressure sufficient to polymerize the olefin with the catalyst system comprising (A) a monocyclopentadienyl transition metal compound of the formula above, and (B), an activator selected from the group consisting of (1) alumoxanes, (2) a salt of a labile, relatively noncoordinating anion that is able to abstract one substituent X from the compound of (A), and (3) a neutral Lewis acid that is able to abstract one substituent X from the compound of (A), and (ii) recovering the polyolefin.

The process according to the present invention is preferably conducted at a temperature between 0° C. and 300° C., a pressure between 1 atmosphere and 1500 atmospheres, and with a reaction time between 1 second and 12 hours.

The catalyst system according to the present invention can also be supported on appropriate inert materials. The support is preferably selected from a group consisting of silica, alumina, carbon black, prepolymer, and magnesium oxide.

The process according to the present invention is for the polymerization of α-olefins, cyclic olefins, dienes, and vinyl aromatic monomers. An α-olefin is preferred with the $C_2$–$C_8$ α-olefins being more preferred. In the process according to the present invention the polymers produced can be homopolymers, copolymers of two olefin monomers, and terpolymers of three or more olefin monomers. For homopolymers, an α-olefin is preferred with the $C_2$–$C_8$ α-olefins being more preferred. Copolymers are preferably produced from ethylene and a $C_3$–$C_8$ α-olefin, or propylene and a $C_2$–$C_8$ α-olefin. Terpolymers are preferably produced from ethylene and/or propylene and one or two other $C_2$–$C_8$ α-olefins. The most preferred polyolefins produced according to the present invention are the hexene linear low-density polyethylenes, since this type of catalyst is particularly useful in the preparation thereof.

The monocyclopentadienyl transition metal compound according to the present invention can be prepared by a number of general and well known metathetical methods. For example, transition metal halides can be reacted with trimethylsilyl or tributylstannyl derivatives of the cyclopentadiene to form the monocyclopentadienyl transition metal compound and chlorotrimethylsilane or chlorotributylstannane. Transition metal halides or alkoxides can also be reacted with alkali metal (Li, Na, K) or thallium salts of the cyclopentadienyl ring, forming the monocyclopentadienyl transition metal compound and an alkali metal halide, an alkali metal alkoxide, or thallium halide.

The catalyst system used in the polymerization process of the present invention can produced by the general process of combining the components in any order.

The following examples are intended to illustrate the present invention, and are not intended to be a limitation upon the reasonable scope thereof.

EXAMPLES

Example 1

This example illustrates the preparation of the monocyclopentadienyl transition metal compound.

All reactions were carried out under an argon atmosphere using standard Schlenk techniques. All chemicals were purchased from Aldrich. Solvents were distilled over Na/K alloy or $CaH_2$ prior to use. $^1HNMR$ spectra were recorded on a Varian XL 200-MHz FT spectrometer. Chemical shifts are reported in δ units referenced to tetramethylsilane.

a) (2-dimethylaminoethyl) cyclopentadiene was synthesized by a modification of a literature procedure as disclosed in *J. Organomet. Chem.*, Vol. 423, p. 31, 1992. 2-Chloro-1-(dimethylamino) ethane (43.04 g, 400 mmol) free of hydrogen chloride was added slowly to a stirred suspension of cyclopentadienyllithium in THF/hexane (1:1) (obtained from the reaction of n-butyllithium (250 ml, 1.6M in hexane) with freshly distilled cyclopentadiene (33.0 ml, 400 mmol) in THF (250 ml) at 0° C. and the reaction mixture refluxed overnight. Filtration of the lithium chloride, removal of the solvents, and a trap-to-trap distillation at reduced pressure afforded (2-dimethylaminoethyl) cyclopentadiene as a colorless liquid (53.58 g, 98%).

b) Treatment of (2-dimethylaminoethyl) cyclopentadiene (32.24 g, 236 mmol) with n-butyllithium (148 ml, 1.6M in hexane) in THF (150 ml) at 0° C. and subsequent reaction with chlorotrimethylsilane (30 ml, 236 mmol) at 0° C. for 4 hours followed by filtration of the precipitate, removal of the volatiles, and distillation at reduced pressure (51–52° C., $5\times10^{-3}$ mm Hg) afforded at least three isomers of (2-dimethylaminoethyl)cyclopentadienyltrimethylsilane as a pale yellow liquid (44.12 g, 89%). $^1H$ NMR ($CDCl_3$) δ 6.70–6.05 (m, ring H), 3.28 (br s, ring H), 3.07–2.85 (m, ring H), 2.65–2.37 (m, 4H, $CH_2CH_2N(CH_3)_2$), 2.28 (s, major isomer), 2.27 (s) [6H, $N(CH_3)_2$], 0.14 (s), 0.13 (s), –0.04 (s, major isomer).

c) Reaction of (2-dimethylaminoethyl) cyclopentadienyltrimethylsilane (8.90 g, 42.5 mmol) with titanium tetrachloride (8.06 g, 42.5 mmol) in dichloromethane at –78° C., followed by removal of the solvent and washing with pentane (2×100 ml), led to the formation of (2-dimethylaminoethyl)cyclopentadienyltitanium trichloride as a yellow powder pure enough for synthetic purposes. An analytically pure sample was obtained by recrystallization from dichloromethane as a yellow-orange microcrystalline solid. $^1H$ NMR ($CDCl_3$) δ 6.97 (t, 2H, $C_5H_4$), 6.88 (t, 2H, $C_5H_4$), 3.26 (t, 2H, J=6.5 Hz, $CH_2N$), 3.06 (t, 2H, J=6.5 Hz, $CH_2$), 2.69 (s, 6H, $N(CH_3)_2$).

Example 2

Polymerization was done in a 250 mL crown-capped pressure bottle sealed under argon and containing a magnetic stir bar sealed under argon. Toluene (50 mL) was added and the argon was evacuated. The bottle was refilled with ethylene at 15 psi, 2.5 mmol MAO was injected and the mixture was stirred 10 minutes at 20° C. 0.4 mg (2-dimethylaminoethyl)cyclopentadienyltitanium trichloride was added and the reaction was stirred 10 minutes. The polymerization was stopped by venting the pressure and adding acidic methanol to the mixture. 0.15 g polyethylene was recovered having a $M_w$ of 300,000.

Example 3

The procedure of Example 2 was substantially repeated except that 5.0 mmol MAO and 0.7 mg (2-dimethylaminoethyl)cyclopentadienyltitanium trichloride were used. 0.56 g polyethylene was recovered having a $M_w$ of 240,000.

Example 4

The procedure of Example 2 was substantially repeated except that 10.0 mmol MAO and 1.4 mg (2-dimethylaminoethyl)cyclopentadienyltitanium trichloride were used. 0.77 g polyethylene was recovered having a $M_w$ of 210,000.

Example 5

Toluene (50 ml) was added to the 250 ml crown-capped glass pressure bottle and the argon was evacuated. The bottle was refilled with propylene at 20 psi, 2.5 mmol MAO was injected and the mixture was stirred 10 minutes at 20° C. 0.4 mg (2-dimethylaminoethyl)cyclopentadienyltitanium trichloride was added and the reaction was stirred 90 minutes. The polymerization was stopped by venting the pressure and adding acidic methanol to the mixture. 0.79 g amorphous polypropylene was recovered having a $M_w$ of 320,000.

Example 6

The procedure of Example 5 was substantially repeated except that 5.0 mmol MAO and 0.7 mg (2-dimentylaminoethyl) cyclopentadienyltitanium thrichloride were used. 3.4 g amorphous polypropylene was recovered having a $M_w$ of 290,000.

Example 7

The procedure of Example 5 was substantially repeated except that 10.0 mmol MAO and 0.7 mg (2-dimethylaminoethyl) cyclopentadienyltitanium trichloride were used and the polymerization was stopped after 30 minutes. 1.85 g amorphous polypropylene was recovered having a $M_w$ of 450,000.

Example 8

The procedure of Example 7 was substantially repeated except that 1.4 mg of (2-dimethylaminoethyl) cyclopentadienyltitanium trichloride was used. 2.66 g amorphous polypropylene was recovered having a $M_w$ of 350,000.

Example 9

The procedure of Example 8 was substantially repeated except that 20.0 mmol MAO was used. 2.97 g amorphous polypropylene was recovered having a $M_w$ of 340,000.

Example 10

Toluene (50 ml) was added to the 250 ml crown-capped glass pressure bottle and the argon was evacuated. The bottle was refilled with propylene at 20 psi, 0.1 mmol triisobutylaluminum was injected and 1.4 mg (2-dimethylaminoethyl) cyclopentadienyltitanium trichloride was added. The mixture was stirred five minutes at 20° C., then 4.6 mg triphenylcarbenium tetrakis (pentafluorophenyl)borate was added. The polymerization was stopped after 7 minutes by venting the pressure and adding acidic methanol to the mixture. 2.19 g amorphous polypropylene was recovered having a $M_w$ of 450,000.

Comparative Example 1

The procedure of Example 2 was substantially repeated except that 10.0 mmol MAO and 0.5 mg cyclopentadienyltitanium trichloride were used. 10 mg polyethylene was recovered.

Comparative Example 2

The procedure of Example 9 was substantially repeated except that 1.1 mg cyclopendienyltitanium trichloride was used. No amorphous polypropylene was recovered.

Comparative Example 3

The procedure of Example 10 was substantially repeated except that 1.1 mg cyclopentadienyltitanium trichloride was used. No amorphous polypropylene was recovered.

Example 11

The polymerization was done in a jacketed, 3-liter stainless steel autoclave equipped with stirrer, thermocouples, a pressure gauge and inlets for introduction of nitrogen, solvent, monomers, and catalyst. Solvent, monomers, and nitrogen were purified by standard techniques. The autoclave was thoroughly dried and degassed before use.

a) A catalyst solution was prepared by first adding a solution of 250 ul trimethylaluminum in 3 ml toluene to 0.0025 g (2-dimethylaminoethyl) cyclopentadienyltitanium trichloride. The mixture was stirred briefly and a solution of 0.008 g triphenylcarbenium tetrakis(pentafluorophenyl) borate in 3 ml toluene was then added. The mixture was again stirred briefly and then added to a catalyst charging bomb.

b) 1 liter of heptane and a solution of 250 μl trimethylaluminum in 20 ml hexane was added to the autoclave, and the mixture was heated to 80° C. and stirred for 15 minutes. The autoclave was then pressurized to 200 psi with ethylene and the catalyst solution was injected. A 4° C. exotherm was observed on adding the catalyst solution to the autoclave. After 1 hour at 80° C. and 200 psi ethylene the polymerization was stopped by rapidly cooling and venting the autoclave. 65 g of polyethylene was recovered having a melt index of 0.20 g/10 min. and a density of 0.956 at 23° C.

Example 12

The procedure of Example 12 was substantially repeated except the autoclave was charged with 800 ml heptane and 200 ml 1-hexene instead of 1 liter heptane. 110 g of copolymer was recovered having a $M_w$ of 88,000 and a molecular weight distribution ($M_w/M_n$) of 2.06. The copolymer had a melt index of 2.58 g/10 minutes, a density of 0.921 at 23° C. and contained 6.9 wt % 1-hexene by $^{13}$CNMR.

Comparative Example 4

The procedure of Example 12 was substantially repeated except that 0.0019 g cyclopentadienyltitanium trichloride was used in place of (2-dimethylaminoethyl) cyclopentadienyltitanium trichloride. 16 g of polyethylene was recovered having a melt index of 0.03 g/10 minutes and a density of 0.955 at 23° C.

Comparative Example 5

The procedure of Example 12 was substantially repeated except that 0.0025 g pentamethylcyclopentadienyltitanium trichloride was used in place of (2-dimethylaminoethyl) cyclopentadienyltitanium trichloride. 24 g of polyethylene was recovered having a melt index of 0.15 g/10 min. and a density of 0.952 at 23° C.

TABLE 1

| | Monomer Pressure | (Monomer) | (Catalyst) | (MAO) | (borate) | (Al):(Ti) | Polymerization Time | Yield (g) | Activity (× 10⁶) | $M_w$ |
|---|---|---|---|---|---|---|---|---|---|---|
| Example 2 | 15 psi ethylene | 0.37M | 24 μM | 50 mM | | 2000 | 10 | 0.15 | 1.98 | 300,000 |
| Example 3 | 15 psi ethylene | 0.37M | 50 μM | 100 mM | | 2000 | 10 | 0.56 | 3.62 | 240,000 |
| Example 4 | 15 psi ethylene | 0.37M | 50 μM | 200 mM | | 4000 | 10 | 0.77 | 4.96 | 210,000 |
| Example 5 | 20 psi propylene | 0.78M | 25 μM | | | 2000 | 90 | 0.79 | 0.54 | 320,000 |
| Example 6 | 20 psi propylene | 0.78M | 50 μM | | | 2000 | 90 | 3.4 | 1.16 | 290,000 |
| Example 7 | 20 psi propylene | 0.78 | 50 μM | | | 4000 | 30 | 1.85 | 1.9 | 450,000 |
| Example 8 | 20 psi propylene | 0.89M | 100 μM | | | 2000 | 30 | 2.66 | 1.37 | 350,000 |
| Example 9 | 20 psi propylene | 0.78M | 100 μM | | | 4000 | 30 | 2.97 | 1.53 | 340,000 |
| Example 10 | 20 psi propylene | 0.78M | 100 μM | 100 mM | | 20 | 30 | 2.19 | 4.82 | 450,000 |
| Comparative Example 1 | 15 psi ethylene | 0.37M | 50 μM | | | | | 0.01 | 0.0062 | |
| Comparative Example 2 | 20 psi propylene | 0.78M | 100 μM | | | | | 0 | 0 | |
| Comparative Example 3 | 20 psi propylene | 0.78 | 100 μM | | 100 mM | 20 | | 0 | 0 | |

We claim:

1. A monocyclopentadienyl metal compound corresponding to the formula:

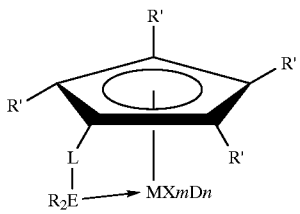

Wherein,

M is a metal selected from the group consisting of titanium, zirconium, and hafnium;

m is one, two, or three, depending on the valency and oxidation state of M;

R' is each independently selected from the group consisting of hydrogen, hydrocarbyl groups, silyl groups, germyl groups, and stannyl groups, including wherein two or more R' groups can be joined to form a ring;

L is a covalent bridging group containing a main group element from Group 14 selected from the group consisting of carbon, silicon, germanium, and tin;

E is datively bonded to M, and is a main group element from Group 15 selected from the group consisting of nitrogen, phosphorous, arsenic, and antimony;

R is independently selected from substituted hydrocarbyl groups, unsubstituted hydrocarbyl groups, and silyl groups, wherein two R-groups can be joined to form a ring, and wherein an R-group and L can be joined to form a ring;

X is each independently selected from the group consisting of hydrogen, halides, substituted hydrocarbyl groups, unsubstituted hydrocarbyl groups, silyl groups, alkoxides, aryloxides, amides, arylamides, phosphides, arylphosphides, carboxylates, and sulfonates;

D is a neutral Lewis base; and n is 0, 1, or 2.

2. The composistion according to claim 1, wherein the monocyclopentadienyl transition metal compound is indenyl of the formula:

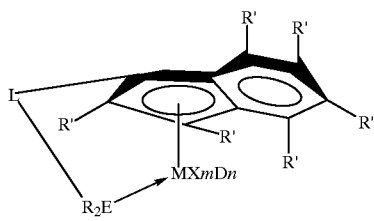

R' is each independently selected from the group consisting of hydrogen, hydrocarbyl group, silyl groups, germyl groups, and stannyl groups, including wherein two or more R' groups can be joined to form a ring.

3. The composition according to claim 1 wherein the monoclyclopentadienyl transition metal compound is fluorenyl and is of the formula:

R' is each independently selected from the group consisting of hydrogen, hydrocarbyl group, silyl groups, germyl groups, and stannyl groups, including wherein two or more R' groups can be joined to form a ring.

4. The composition according to claim 1 wherein M is selected from the group consisting of titanium and zirconium.

5. The composition according to claim 1 wherein R' is each independently selected from the group consisting of hydrogen and $C_1$–$C_4$ alkyls.

6. The composition according to claim 5 wherein at least two R' are hydrogen.

7. The composition according to claim 1 wherein L is a covalent bridging group selected from the group consisting of:

$CR''_3$, $CR''_2 CR''_2$, $CR''_2 CR''_2 CR''_2$, and $CR''=CR''$, wherein R'' is each independently selected from the group consisting of hydrogen, alkyl, and aryl.

8. The composition according to claim 7 wherein L is selected from the group consisting of
, $CR''_2$, $CR''_2 CR''_2$ and $CR''_2 CR''_2 CR''_2$, wherein R'' each is independently selected from the group consisting of hydrogen and methyl.

9. The composition according to claim 8 wherein L is $CH_2 CH_2$.

10. The composition according to claim 1 wherein E is selected from the group consisting of nitrogen and phosphorous.

11. The composition according to claim 10 wherein E is nitrogen.

12. The composition according to claim 1 wherein each R is independently a hydrocarbyl group including where two R-groups are joined to form a ring.

13. The composition according to claim 1 wherein m is three.

14. The composition according to claim 1 wherein X is independently selected from the group consisting of halides and alkoxides.

15. The composition according to claim 14 wherein X is independently selected from the group consisting of chlorine and isopropoxide.

16. The composition according to claim 15 wherein X is chlorine.

17. The composition according to claim 1 wherein n is one or two, and D is selected from the group consisting of ether and tetrahydrofuran.

18. The composition according to claim 1 wherein n=0.

19. The composition according to claim 1 wherein R is each independantly selected from the group consisting of propyl, ethyl and methyl.

20. The composition according to claim 19 wherein R is each independently selected for the group consisting of ethyl and methyl.

* * * * *